(12) United States Patent
Xu

(10) Patent No.: US 7,335,621 B2
(45) Date of Patent: Feb. 26, 2008

(54) CATALYST COMPOSITIONS AND PREPARATION THEREOF

(75) Inventor: Teng Xu, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/713,199

(22) Filed: Mar. 2, 2007

(65) Prior Publication Data

US 2007/0249488 A1 Oct. 25, 2007

Related U.S. Application Data

(60) Provisional application No. 60/793,023, filed on Apr. 19, 2006.

(51) Int. Cl.
*B01J 27/182* (2006.01)
*B01J 29/06* (2006.01)

(52) U.S. Cl. .................. 502/214; 502/73; 502/208

(58) Field of Classification Search ............. 502/73, 502/208, 214
See application file for complete search history.

(56) References Cited

U.S. PATENT DOCUMENTS

| | | |
|---|---|---|
| 4,302,622 A | 11/1981 | Chu |
| 4,440,871 A | 4/1984 | Lok et al. |
| 4,465,889 A | 8/1984 | Anthony et al. |
| 4,499,327 A | 2/1985 | Kaiser |
| 4,590,323 A | 5/1986 | Chu |
| 4,677,242 A | 6/1987 | Kaiser |
| 4,677,243 A | 6/1987 | Kaiser |
| 4,873,390 A | 10/1989 | Lewis et al. |
| 4,929,763 A | 5/1990 | Luetkens, Jr. et al. |
| 5,043,308 A | 8/1991 | Luetkens, Jr. et al. |
| 5,095,163 A | 3/1992 | Barger |
| 5,130,114 A | 7/1992 | Igarashi |
| 5,189,198 A | 2/1993 | Kumazawa et al. |
| 5,714,662 A | 2/1998 | Vora et al. |
| 5,879,647 A | 3/1999 | Wataya et al. |
| 6,017,442 A | 1/2000 | Wu et al. |
| 6,166,282 A | 12/2000 | Miller |
| 6,180,828 B1 | 1/2001 | Hidaka et al. |
| 6,287,527 B1 | 9/2001 | Kawanami et al. |
| 6,600,056 B1 | 7/2003 | Mikawa et al. |
| 6,812,372 B2 | 11/2004 | Janssen et al. |
| 6,844,291 B2 | 1/2005 | Levin et al. |
| 6,906,232 B2 | 6/2005 | Levin et al. |
| 6,951,830 B2 | 10/2005 | Janssen |
| 7,125,821 B2 | 10/2006 | Xu et al. |
| 7,145,051 B2 | 12/2006 | Ou et al. |
| 2003/0171633 A1 | 9/2003 | Xu et al. |
| 2005/0020435 A1 | 1/2005 | Beck et al. |
| 2005/0096214 A1 | 5/2005 | Janssen et al. |
| 2005/0101818 A1 | 5/2005 | Levin et al. |
| 2006/0004240 A1 | 1/2006 | Xu et al. |

FOREIGN PATENT DOCUMENTS

WO  WO 03/074177  9/2003

*Primary Examiner*—Elizabeth D. Wood

(57) ABSTRACT

This invention relates to a process and the product thereof for preparing, a molecular sieve catalyst composition, comprising a mixture of: a first quantity of molecular sieve particles, having an 8-ring or larger structure, and a pore size of from about 3 angstroms to about 15 angstroms; and a second quantity of metal carbonate particles; the mixture having been calcined at a temperature of at least about 200° C. for at least about 1 second.

40 Claims, 1 Drawing Sheet

CATALYST COMPOSITIONS AND PREPARATION THEREOF

CROSS REFERENCE TO RELATED APPLICATIONS

This claims the benefit of and priority from U.S. Ser. No. 60/793,023, filed Apr. 19, 2006. The above application is fully incorporated herein by reference.

FIELD OF THE INVENTION

The present invention relates to molecular sieve compositions and catalysts containing the same, to the synthesis of such compositions and catalysts and to the use of such compositions and catalysts in conversion processes.

BACKGROUND OF THE INVENTION

There are wide varieties of molecular sieves for use in commercial petroleum and petrochemical industry processes. Molecular sieves are porous solids having pores of varying sizes. The most commercially useful molecular sieves are known as zeolites. Zeolites in general have a one-, two- or three-dimensional crystalline pore structure having uniformly sized pores of molecular dimensions that selectively adsorb molecules that can enter the pores, and exclude those molecules that are too large.

Some examples of molecular sieves are aluminosilicates and metalloaluminophosphates, such as silicoaluminophosphates (SAPOs). SAPO molecular sieves contain a three-dimensional microporous crystalline framework structure of [$SiO_4$], [$AlO_4$] and [$PO_4$] corner-sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formation into a catalyst, and its use in a process for converting hydrocarbon feedstock into olefin(s), particularly where the feedstock is methanol, are disclosed in a large number of granted patents and pending patent applications, including for example, U.S. Pat. Nos. 4,499,327, 4,677,242, 4,677,243, 4,873,390, 5,095,163, 5,714,662 and 6,166,282 and U.S. Patent Application Publication Nos. 20050096214 and 20050101818 (all incorporated herein by reference).

Typically, molecular sieves are formed into molecular sieve catalyst compositions to improve their durability in commercial processes. These molecular sieve catalyst compositions are formed by combining the molecular sieve and a matrix material usually in the presence of a binder. The purpose of the binder is to hold the matrix material, often clay, to the molecular sieve. Binders and matrix materials typically only serve to provide desired physical characteristics to the catalyst composition, and have little to no effect on conversion and selectivity of the molecular sieve.

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

Alternately, the methanol-to-olefins (MTO) process can be used to produce light olefins by contacting a feedstock containing oxygenated organic compounds, such as methanol or dimethyl ether (DME), with a molecular sieve catalyst, such as a SAPO molecular sieve. Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor.

Many attempts have been made to improve a molecular sieve catalyst composition's selectivity and/or extend its lifetime by modifying the catalyst composition. For example, U.S. Pat. No. 6,180,828 discusses the use of a modified molecular sieve to produce methylamines from methanol and ammonia where, for example, a silicoaluminophosphate molecular sieve is combined with one or more modifiers, such as zirconium oxide, a titanium oxide, yttrium oxide, montmorillonite or kaolinite.

U.S. Pat. No. 4,465,889 describes a catalyst composition comprising a silicate molecular sieve impregnated with thorium, zirconium, or titanium metal oxide for use in converting methanol, dimethyl ether, or a mixture thereof into a hydrocarbon product rich in iso-$C_4$ compounds.

U.S. Pat. No. 6,906,232 relates to a conversion process of a feedstock, preferably an oxygenated feedstock, into one or more olefin(s), preferably ethylene and/or propylene, in the presence of a molecular sieve catalyst composition that includes a molecular sieve and a Group 3 metal oxide and/or an oxide of a Lanthanide or Actinide series element. The invention is also directed to methods of making and formulating the molecular sieve catalyst composition useful in a conversion process of a feedstock into one or more olefin(s).

Other patents and publications of relevance to this invention include:

U.S. Pat. No. 6,906,232, U.S. Pat. No. 6,844,291, U.S. Pat. No. 6,951,830,

U.S. Pat. No. 4,302,622, U.S. Pat. No. 4,590,323, U.S. Pat. No. 4,929,763,

U.S. Pat. No. 5,043,308, U.S. Pat. No. 5,130,114, U.S. Pat. No. 5,189,198,

U.S. Pat. No. 6,017,442, U.S. Pat. No. 6,287,527, U.S. Pat. No. 6,600,056,

EP 1478464 U.S. Patent Pub. No. 20030171633, U.S. Patent Pub. No. 20030181325, U.S. Patent Pub. No. 20050054517 and U.S. Patent Pub. No. 20050020435.

Molecular sieve catalysts, including SAPO molecular sieve catalysts, when used to convert methanol to olefins, require frequent regeneration due to coking and therefore have limited lifetimes. Coking occurs when coke deposits either directly (site coverage) and/or indirectly (pore blockage) decrease the number of active sites available for the conversion reaction in the reactor. Coking is a common cause of catalyst deactivation, thereby decreasing catalyst lifetime.

Regeneration is the process whereby at least a portion of the molecular sieve's initial activity is recovered by combusting and removing at least a portion of the coke deposits on the catalyst with agents such as air, hydrogen, steam, or carbon monoxide, alone or in combination. This process is very expensive, time consuming and adds extra steps to the conversion process. It would be beneficial to reduce coking, thereby increasing catalyst lifetime and reducing the need for regeneration, which would decrease the cost of the entire conversion process. Therefore, any means for reducing coke selectivity or increasing catalyst lifetime would result in significant investment savings.

It would also be desirable to have an improved molecular sieve catalyst composition for use in MTO processes having a better conversion rate, improved olefin selectivity and a longer lifetime.

The present invention satisfies these needs by providing a molecular sieve catalyst composition and a method for preparing the molecular sieve catalyst composition in which a metal carbonate is mixed with the molecular sieve followed by calcination of the mixture. In a preferred embodiment, the catalyst composition is prepared by mixing a metal carbonate with a molecular sieve catalyst, for example SAPO-34, followed by calcination. This results in significantly longer catalyst lifetime when compared with a molecular sieve catalyst composition with no metal carbonate. Also the calcination temperature used has a profound impact on coke selectivity, and catalyst lifetime.

SUMMARY OF THE INVENTION

In a first aspect, this invention relates to a catalyst composition prepared according to a process comprising the steps of: mixing a first quantity of molecular sieve particles with a second quantity of metal carbonate particles, the molecular sieve particles having, an 8-ring or larger structure, and a pore size of from about 3 angstroms to about 15 angstroms; and calcining the mixture of molecular sieve particles and metal carbonate particles at a temperature of at least about 200° C. for at least 1 second.

In another aspect, this invention also relates to a process for preparing a molecular sieve catalyst composition comprising: mixing a first quantity of molecular sieve particles with a second quantity of metal carbonate particles, the molecular sieve particles having an 8-ring or larger structure, and a pore size of from about 3 angstroms to about 15 angstroms, and calcining the molecular sieve and metal carbonate mixture at a temperature of at least about 200° C. for at least 1 second.

In yet another aspect, this invention further relates to a molecular sieve catalyst composition comprising a mixture of: a first quantity of molecular sieve particles, an 8-ring or larger structure, and a pore size of from about 3 angstroms to about 15 angstroms; and a second quantity of metal carbonate particles having an average particle size of less than about 500 microns; the mixture having been calcined at a temperature of at least about 200° C. for at least about 1 second.

DESCRIPTION OF THE DRAWING

The FIGURE shows the Cumulative Methanol Converted per gram of Sieve (CMCPS) for each of the Examples as described below.

DETAILED DESCRIPTION OF THE INVENTION

Definitions

Figure 1:
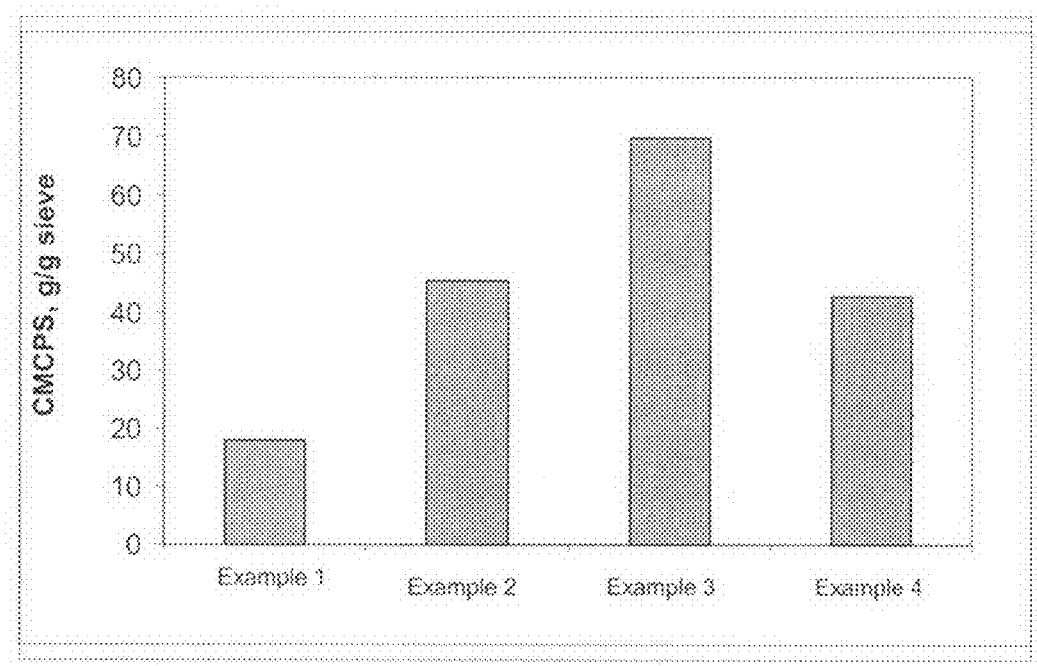

As used herein, "molecular sieve particles" are defined to include both particles of the crystalline molecular sieve alone and particles of a molecular sieve catalyst composition in which the crystalline molecular sieve has been combined with other materials such as matrix material and/or a binder.

As used herein, "intimate mixture" is defined to be a complete intermixture in which one substance is uniformly distributed in a finely divided state throughout a second substance.

As used herein, "calcination" is the heating of a solid to a temperature below its melting point to bring about a state of thermal decomposition or a phase transition other than melting.

As used herein, the "Lifetime Enhancement Index" or "LEI" is defined as the ratio of the lifetime of a molecular sieve catalyst composition comprising molecular sieve particles mixed with metal carbonate particles and calcined according to the present invention, compared to that of the same molecular sieve particles alone, defined as having an LEI of 1.

In a preferred embodiment, this invention relates to a catalyst composition prepared according to a process comprising the steps of: mixing a first quantity of molecular sieve particles with a second quantity of metal carbonate particles, the molecular sieve particles having an 8-ring or larger structure, and a pore size of from about 3 angstroms to about 15 angstroms; and calcining the mixture of molecular sieve particles and metal carbonate particles at a temperature of at least about 200° C. for at least 1 second.

Molecular Sieve

Molecular sieves have various chemical, physical, and framework characteristics and have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves, for which a structure has been established, are assigned a three letter code and are described in the *Atlas of Zeolite Framework Types*, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AEI, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Crystalline molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the molecular sieves used in the present invention have 8-, 10- or 12-ring structures or larger and a pore size in the range of from about 3 Å to about 15 Å. The pore sizes of the molecular sieves are substantially uniform. Therefore as referred to herein, when only one number is mentioned as the pore size of the molecular sieve, minor variations of that pore size are acceptable. In a preferred embodiment of this invention, the molecular sieves, preferably silicoaluminophosphate molecular sieves, have 8-rings and a pore size of from about 3 Å to about 15 Å, more preferably from 3 Å to about 10 Å, even more preferably from about 3 Å to about 8 Å, still more preferably from 3 Å to about 4.5 Å, and most preferably from 3.5 Å to about 4.2 Å.

Molecular sieves have a molecular framework of one, preferably two or more corner-sharing [$TO_4$] tetrahedral units, more preferably, two or more [$SiO_4$], [$AlO_4$] and/or [$PO_4$] tetrahedral units, and most preferably [$SiO_4$], [$AlO_4$] and [$PO_4$] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO), EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves which may be used in connection with this invention include those described in R. Szostak, *Handbook of Molecular Sieves*, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (AlPO) molecular sieves and silicoaluminophosphate (SAPO) molecular sieves and substituted, preferably metal substituted, AlPO and SAPO molecular sieves. The most preferred molecular sieves are SAPO molecular sieves, and metal substituted SAPO molecular sieves.

Non-limiting examples of SAPO and ALPO molecular sieves useful in connection with the present invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing forms thereof. Preferably, the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. The more preferred zeolite-type molecular sieves include one or a combination of SAPO-18, SAPO-34, SAPO-35, SAPO-44, SAPO-56, ALPO-18 and ALPO-34, and metal containing forms thereof, even more preferably one or a combination of SAPO-18, SAPO-34, ALPO-34 and ALPO-18, and metal containing forms thereof, and most preferably one or a combination of SAPO-34 and ALPO-18, and metal containing forms thereof. Optionally, the molecular sieve is selected from the group consisting of SAPO-34, the metal containing forms thereof. Another important class of SAPO molecular sieves consists of mixed or intergrown phases of molecular sieves having the CHA and AEI framework types. Examples of such materials are disclosed in WO 98/15496, published 16 Apr. 1998, in WO 02/070407, published Sep. 12, 2002, and U.S. Pat. No. 6,812,372, all herein fully incorporated by reference.

Each of the crystalline molecular sieves may be used singly or in a mixture with other molecular sieves. This may be not only as a simple mixture, but as an intergrowth, for example, of offretite and erionite as in U.S. Pat. No. 4,086,186, namely an intergrowth of two kinds of crystalline molecular sieves having different topologies from each other.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from Groups 1-12 and the Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. All numbers and references to the Periodic Table of Elements are based on the new notation as set out in *Chemical and Engineering News*, 63(5), 27 (1985). For the purposes of the present invention, a "templating agent" is any substance as a result of which the solid which is formed during generation of the at least one material from the synthesis mixture has at least one type of pore (micropores, mesopores, macropores).

In another embodiment, m is from about 0.1 to about 1, x is from about 0.01 to about 0.25, y is from about 0.4 to about 0.5, and z is in the range of from about 0.25 to about 0.5, more preferably m is from about 0.15 to about 0.7, x is from about 0.01 to about 0.2, y is from about 0.4 to about 0.5, and z is from about 0.3 to about 0.5.

Templating agents are generally compounds that contain elements of Group 15 of the Periodic Table of Elements, particularly nitrogen, phosphorus, arsenic and antimony, more preferably nitrogen or phosphorous, and most preferably nitrogen. Typical templating agents of Group 15 of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds. Non-limiting examples of templating agents can be found in U.S. Pat. No. 6,906,232, column 8, lines 6-43, incorporated herein by reference.

In another embodiment, the molecular sieve is an intergrowth material having two or more distinct phases of crystalline structures within one molecular sieve composition. In particular, intergrowth molecular sieves are described in the U.S. Patent Application Pub. No. 2002/0165089 and PCT WO 98/15496 published Apr. 16, 1998, both of which are herein fully incorporated by reference. For example, SAPO-18, AlPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the ratio of CHA to AEI is greater than 1:1 as determined by the DIFFaX method disclosed in U.S. Pat. No. 6,812,372.

The molecular sieve, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols (dispersions of small solid particles in a liquid), and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, is subjected to well known modification processes such as calcination and/or acid treatment and/or chemical treatment.

In one preferred embodiment, the matrix material is a clay or a clay-type composition, preferably a clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm. As used herein, average particle size is measured by Atomic Force Microscopy (AFM).

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco™ 8676 available from Nalco Chemical Co., Naperville, Ill., and Nyacol™ available from The PQ Corporation, Valley Forge, Pa.

In one embodiment, the binder, templating agent and the molecular sieve and the matrix material are combined to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:5 to 1:15, more preferably 1:4 to 1:10, and most preferably 1:5 to 1:6. It has been found that a higher sieve content, lower matrix content, increases the molecular sieve catalyst composition performance; however, lower sieve content, higher matrix material, improves the attrition resistance of the composition.

The molecular sieve and matrix material, and the optional binder, are combined in any order, together, simultaneously, sequentially, or a combination thereof.

In an embodiment, the average particle size of the molecular sieve particles is preferably less than about 300 microns, more preferably less than about 200 microns and most preferably less than about 150 microns.

In an embodiment, the pore size of the molecular sieve is from about 3 angstroms to about 15 angstroms, more preferably less than about 12 Å, more preferably less than about 10 Å, more preferably less than about 8 Å, more preferably less than about 6 Å, more preferably in the range of from 3 Å to about 5 Å, more preferably from 3 Å to about 4.5 Å, and most preferably from 3.5 Å to about 4.2 Å. Pore size can be determined by procedures known to those skilled in the art.

In an embodiment, structure of the molecular sieve is 8-ring or larger, more preferably an 8-, 10-, or 12-ring structure, and most preferably an 8-ring structure.

Metal Carbonate

In a preferred embodiment, the metal carbonate comprises a metal chosen from groups 2, 3, 4, 8, 9, or 10 of the periodic table, more preferably from groups 2 and 3, more preferably from group 3, and most preferably the metal carbonate is yttrium carbonate. In another embodiment, the average particle size of the metal carbonate is preferably less than about 2 mm, more preferably less than about 1 mm, more preferably less than 0.5 mm, more preferably less than about 450 microns, more preferably less than about 400 microns, more preferably less than about 350 microns, and most preferably less than about 300 microns as measured by a Microtrac particle size analyzer, model S3000, commercially available from the Microtrac Inc., Montgomeryville, Pa.

Process

Intimate Mixing

In a preferred embodiment, the molecular sieve, as discussed above, in solid particulate form is intimately mixed with the metal carbonate, as discussed above, also in solid particulate form. Intimate mixing can be achieved by any method known in the art, such as mixing with a mixer muller, mortar and pestle, drum mixer, ribbon/paddle blender, kneader, or the like. Chemical reaction between the molecular sieve and the metal oxide(s) is unnecessary and, in general, is not preferred.

Calcination

Once the molecular sieve catalyst composition is formed in a substantially dry or dried state, to further harden and/or activate the formed catalyst composition, a heat treatment such as calcination, at an elevated temperature is usually performed. Typical calcination environments are air (which may include a small amount of water vapor), nitrogen, helium, flue gas (combustion product lean in oxygen), or any combination thereof. A conventional calcination environment to harden the catalyst particles is air that typically includes a small amount of water vapor.

In a preferred embodiment of the invention, the molecular sieve catalyst composition is calcined for at least about one second at a temperature of preferably less than about 700° C., more preferably less than about 650° C., more preferably less than about 600° C., more preferably less than about 550° C., and most preferably less than about 500° C. In a preferred embodiment the molecular sieve catalyst composition is calcined at a temperature of preferably at least about 200° C., more preferably at least about 250° C., more preferably at least about 300° C., more preferably at least about 350° C., and most preferably at least about 400° C.

Calcination of the formulated molecular sieve catalyst composition maybe carried out in any of a number of well known devices including rotary calciners, fluid bed calciners, batch ovens, and the like. Calcination time is typically dependent on the degree of hardening of the molecular sieve catalyst composition and the temperature.

In a preferred embodiment, the catalyst composition is heated in nitrogen at a temperature of less than 700° C., more preferably less than 650° C., more preferably less than 600° C., more preferably less than 550° C., and most preferably less than 500° C. Heating is carried out for a period of time typically from 30 seconds to 15 hours, such as from 1 hour to about 10 hours, for example from about 1 hour to about 5 hours, and particularly from about 2 hours to about 4 hours.

When a templating agent is used in the synthesis of a molecular sieve, it is preferred that the templating agent is substantially, preferably completely, removed after crystallization by numerous well known techniques, for example, heat treatments such as calcination to either partially or completely decompose and oxidize the templating agent.

EXAMPLES

In order to provide a better understanding of the present invention including representative advantages thereof, the following Examples are offered.

Materials Used

In the examples below, yttrium carbonate ($Y_2(CO_3)_3$), silicon-carbide, and SAPO-34 molecular sieve were used.

Test Methods

For the purpose of determining LEI, lifetime is defined as the cumulative amount of methanol converted, preferably into one or more olefin(s), per gram of molecular sieve (CMCPS), until the conversion drops to about 10 wt %. If the conversion has not fallen to 10 wt % of its initial value by the end of the experiment, lifetime is estimated by linear extrapolation based on the rate of decrease in conversion over the last two data points in the experiment. For the purposes of determining the LEI for the following examples in a preferred oxygenate conversion process, methanol is converted to one or more olefin(s) at 475° C., 25 psig (172 kPag) and a methanol weight hourly space velocity of 100 $h^{-1}$.

To obtain reliable and representative data for the products of the MTO reaction process it was necessary to take the weighted average of the selectivity. The weighted averages in Table 1 were calculated based on the following formula, $x1*y1+(x2-x1)*y2+(x3-x2)*(y2+y3)/2+(x4-x3)*(y3+y4)/2+\ldots$, where xi is yield and yi is grams of methanol fed per grams of sieve. Weight hourly space velocity (WHSV) was reported based on the weight of the sieve. Methanol converted at less than about 10 wt % conversions was not counted in the calculations. Dimethyl ether (DME) was counted as unreacted methanol in calculating methanol conversion for determining CMCPS. Selectivities were calculated by normalizing the yield data excluding methanol and DME.

The collected effluent samples were analyzed by on-line gas chromatography (Hewlett Packard 6890) equipped with a flame ionization detector. The chromatographic column used was a Q-column.

Catalytic performance of the molecular sieve catalyst composition for conversion of methanol was measured using a micro-reactor unit. All examples used a microflow reactor. Typically, about 115 mg of the catalyst composition was mixed with 1 g of 100-µm silicon-carbide. The mixture was loaded into the reactor, which is made of ¼ inch (about 0.635 cm) silicon-steel tubing. The reactor temperature was increased to and then held at 475° C. while the catalyst was under helium flow (46 ml/min) for about 30 to 40 minutes for the temperature to stabilize. Methanol was introduced into the catalyst at 80 µl/min at a WHSV of 100 $h^{-1}$, and a pressure of 25 psig (about 172 kPag) while the effluent was sampled by a 16-loop Valco valve. Typically, 9 to 15 samples were analyzed to obtain the weighted average selectivity.

Example 1

In Example 1, the catalyst composition was a pre-calcined SAPO-34 molecular sieve prepared as described in U.S. Pat. No. 6,812,372, Example 1, column 15, line 33. The calcined SAPO-34 contained about 22 wt % of adsorbed water.

Example 2

In this example, the catalyst composition was prepared by intimately mixing yttrium oxide with SAPO-34, prepared as described in Example 1, with a mortar and pestle. The sample contained about 24 wt % yttrium oxide.

Example 3

In this example, the catalyst composition was prepared by mixing about 6.0140 g of SAPO-34, prepared as described in Example 1, with 2.3469 grams of yttrium carbonate $Y_2(CO_3)_3$. The physical mixture was ground and mixed with a mortar and pestle for about 30 minutes. A portion of the sample was packed directly into the MTO reactor for the lifetime test. The sample was calcined at 475° C. and contained about 19 wt % yttrium.

Example 4

This example was prepared as described above in Example 3, except that the sample was calcined at 700° C. The catalyst composition contained about 19 wt % yttrium.

As shown in the table below, Examples 2, 3 and 4 were prepared to contain the same amount (19 wt %) of yttrium.

TABLE 1

| Example | Calcination Temp. (° C.) | Yttrium wt % | $C_1°$ wt % | $C_2^=$ wt % | $C_2°$ wt % | $C_3^=$ wt % | $C_3°$ wt % | Coke wt % | $C_{4\&+}$ wt % | $C_{2+3}^=$ wt % | CMCPS (g/g) | LEI |
|---|---|---|---|---|---|---|---|---|---|---|---|---|
| 1 | — | 0 | 1.6 | 38.0 | 0.4 | 40.4 | 0.6 | 1.5 | 17.6 | 78.4 | 17.7 | 1.0 |
| 2 | — | 19 | 1.8 | 34.3 | 0.3 | 43.0 | 0.4 | 0.9 | 19.3 | 77.3 | 45.5 | 2.6 |
| 3 | 475 | 19 | 2.1 | 31.0 | 0.2 | 43.2 | 0.5 | 0.4 | 22.5 | 74.2 | 69.7 | 3.9 |
| 4 | 700 | 19 | 2.1 | 34.4 | 0.3 | 43.0 | 0.5 | 0.8 | 18.9 | 77.4 | 42.6 | 2.4 |

Results

Table 1 is a summary of performance data for the various catalyst compositions of Examples 1-4. The performance was measured at a temperature of 475° C., a pressure of 25 psig (about 172 kPag) and WHSV of 100 hour$^{-1}$. The column headers, $C_1$, $C_2^=$, $C_{2°}$, $C_3^=$, $C_{3°}$, $C_{4\&+}$ and $C_{2+3}^=$, refer to methane, ethylene, ethane, propene, propane, hydrocarbons containing 4 or more carbons, and combined ethylene and propene, respectively. The CMCPS and LEI columns refer to the measurements as described above.

The attached figure shows comparative molecular sieve catalyst lifetimes (LEI) for the four molecular sieve catalyst compositions of Examples 1-4. The FIG. clearly shows that the molecular sieve catalyst compositions prepared using yttrium carbonate, Examples 3 and 4, are comparable or better in increasing molecular sieve catalyst lifetime to the yttrium oxide intimate mixture of Example 2. Example 3 showed especially marked improvement over Example 2.

The temperature at which the catalyst compositions containing yttrium carbonate were calcined had a significant impact on the lifetime of the catalyst. The catalyst composition calcined at 475° C. shows a LEI of 3.9, which is a 50% improvement over that of the catalyst composition calcined at 700° C., whose LEI was 2.6.

Catalytic performance of the catalyst composition of Example 1 for conversion of methanol was evaluated using the process described above and showed a CMCPS of 17.7 g-methanol/g-molecular sieve, Example 2 a CMCPS of 45.5 g-methanol/g-molecular sieve, Example 3 a CMCPS of 69.7 g-methanol/g-molecular sieve, and Example 4 a CMCPS of 42.6 g-methanol/g-molecular sieve. The CMCPS values for Examples 3 and 4, comprising the yttrium carbonate, are comparable to or better than Examples 1 and 2, respectively.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby.

What is claimed is:

1. A catalyst composition prepared according to a process comprising the steps of:
   a. mixing a first quantity of molecular sieve particles with a second quantity of metal carbonate particles, the molecular sieve particles having an 8-ring or larger structure, and a pore size of from about 3 angstroms to about 15 angstroms; and
   b. calcining the mixture of molecular sieve particles and metal carbonate particles at a temperature of at least about 200° C. for at least 1 second.

2. The catalyst composition of claim 1, wherein the molecular sieve particles have a pore system defined by an 8-membered ring of tetrahedra [TO$_4$].

3. The catalyst composition of claim 1, wherein the molecular sieve particles have a pore system defined by a 10-membered ring of tetrahedra [TO$_4$].

4. The catalyst composition of claim 1, wherein the molecular sieve particles are silicoaluminophosphate molecular sieve particles and/or aluminosilicate molecular sieve particles, or mixtures thereof.

5. The catalyst composition of claim 1, wherein the molecular sieve particles are of the CHA and/or AEI framework types, or mixtures thereof.

6. The catalyst composition of claim 1, wherein the molecular sieve particles have an average particle size of less than about 2 mm.

7. The catalyst composition of claim 1, wherein the molecular sieve particles have an average particle size of less than about 1 mm.

8. The catalyst composition of claim 1, wherein the molecular sieve particles have an average particle size of less than about 500 microns.

9. The catalyst composition of claim 1, wherein the molecular sieve particles have an average particle size of less than about 150 microns.

10. The catalyst composition of claim 1, wherein the metal carbonate particles comprise about 5 to about 50 wt % of the final mixture of molecular sieve particles and metal carbonate particles.

11. The catalyst composition of claim 1, wherein the mixture has been calcined at a temperature of from about 200° C. to about 700° C. for at least about 1 second.

12. The catalyst composition of claim 1, wherein the mixture has been calcined at a temperature of less than about 500° C. for at least about 1 second.

13. The catalyst composition of claim 1, wherein the mixture has been calcined at a temperature of from about 300° C. to about 600° C. for at least about 1 second.

14. The catalyst composition of claim 1, wherein the mixture has been calcined at a temperature of from about 400° C. to about 600° C. for at least about 1 second.

15. The catalyst composition of claim 1, wherein the molecular sieve particles are SAPO-34.

16. The catalyst composition of claim 1, wherein the metal carbonate comprises a metal selected from the group consisting of groups 2A, 3B, 4B, and 8B of the Periodic Table and combinations thereof.

17. The catalyst composition of claim 1, wherein the metal carbonate is yttrium carbonate.

18. The catalyst composition of claim 1, wherein the molecular sieve particles are SAPO-34 and the metal carbonate is yttrium carbonate.

19. The catalyst composition of claim 17, wherein the molecular sieve particles and the yttrium carbonate particles are intimately mixed.

20. The catalyst composition of claim 1, wherein the molecular sieve particles are SAPO-34, the metal carbonate is yttrium carbonate, the SAPO-34 and the yttrium carbonate are intimately mixed, and the mixture is calcined at about 300° C. to about 600° C. for at least 1 second.

21. The catalyst composition of claim 1, wherein the molecular sieve particles have a pore size of about 3 to about 10 angstroms.

22. The catalyst composition of claim 1, wherein the molecular sieve particles have a pore size of about 3 to about 8 angstroms.

23. The catalyst composition of claim 1, wherein the molecular sieve particles have a pore size of about 3 to about 4.5 angstroms.

24. The catalyst composition of claim 1, wherein the molecular sieve particles have a pore size of about 3.5 to about 4.2 angstroms.

25. The catalyst composition of claim 1, wherein the average particle size of the metal carbonate particles are less than about 500 microns.

26. The catalyst composition of claim 1, wherein the average particle size of the metal carbonate particles are less than about 450 microns.

27. The catalyst composition of claim 1, wherein the average particle size of the metal carbonate particles are less than about 400 microns.

28. The catalyst composition of claim 1, wherein the average particle size of the metal carbonate particles are less than about 350 microns.

29. The catalyst composition of claim 1, wherein the average particle size of the metal carbonate particles are less than about 300 microns.

30. The catalyst composition of claim 1, wherein the molecular sieve particles are crystalline silicoaluminophosphate molecular sieve particles substantially of CHA framework type.

31. The catalyst composition of claim 1, wherein the molecular sieve particles are SAPO molecular sieve particles which consist of mixed or intergrown phases of molecular sieves having the CHA and/or AEI framework types.

32. A process of preparing a molecular sieve catalyst composition comprising:
   a. mixing a first quantity of molecular sieve particles with a second quantity of metal carbonate particles, the molecular sieve particles having an average particle size of less than about 300 microns, an 8-ring or larger structure, and a pore size of from about 3 angstroms to about 15 angstroms, and the metal carbonate particles having an average particle size of less than about 500 microns; and
   b. calcining the molecular sieve and metal carbonate mixture at a temperature of at least about 200° C. for at least 1 second.

33. A catalyst composition comprising a mixture of:
   a. a first quantity of molecular sieve particles having an average particle size of less than about 300 microns, an 8-ring or larger structure, and a pore size of from about 3 angstroms to about 15 angstroms; and
   b. a second quantity of metal carbonate particles having an average particle size of less than about 500 microns; the mixture having been calcined at a temperature of at least about 200° C. for at least about 1 second.

34. The process of claim 32, wherein the molecular sieve particles are SAPO molecular sieve particles which consist of mixed or intergrowth phases of molecular sieves having the CHA and AEI framework types.

35. The process of claim 32, wherein the molecular sieve particles have a pore system defined by an 8-membered ring of tetrahedra [TO$_4$].

36. The process of claim 32, wherein the metal carbonate particles comprise about 5 to about 50 wt % of the final mixture of molecular sieve particles and metal carbonate particles.

37. The process of claim 32, wherein the mixture has been calcined at a temperature of from about 200° C. to about 700° C. for at least about 1 second.

38. The process of claim 32, wherein the metal carbonate comprises a metal selected from the group consisting of groups 2, 3, 4, 8, 9, and 10 of the Periodic Table and combinations thereof.

39. The process of claim 32, wherein the molecular sieve particles are SAPO-34 and the metal carbonate is yttrium carbonate.

40. The process of claim 32, wherein the metal carbonate particles having an average particle size of less than about 400 microns.

* * * * *